:::
United States Patent [19]

Pohmer et al.

[11] Patent Number: 5,424,474

[45] Date of Patent: Jun. 13, 1995

[54] FLUORINATED CARBOXYLIC ACID ESTERS OF PHOSPHONO- AND PHOSPHINOCARBOXYLIC ACIDS CONTAINING HYDROXYL AND/OR MERCAPTO GROUPS, A METHOD FOR THEIR PREPARATION, AND THEIR USE

[75] Inventors: Klaus Pohmer, Köln; Rainer Weber, Odenthal; Hans-Dieter Block; Hans-Heinrich Moretto, both of Leverkusen, all of Germany

[73] Assignee: Bayer AG, Leverkusen, Germany

[21] Appl. No.: 172,274

[22] Filed: Dec. 23, 1993

[30] Foreign Application Priority Data

Jan. 14, 1993 [DE] Germany .................. 43 00 800.3

[51] Int. Cl.⁶ .................. C07F 9/30; C07F 9/38
[52] U.S. Cl. .................. 558/45; 558/166; 558/169; 558/170; 558/172; 558/173; 558/180; 558/191; 558/196; 558/198; 558/203; 558/204; 558/207; 558/214; 560/25; 560/29; 560/33; 560/45; 560/49; 560/60; 560/81; 560/87; 560/88; 560/105; 560/129; 560/160; 560/171; 560/180; 560/197
[58] Field of Search .................. 558/45, 166, 169, 170, 558/172, 173, 180, 191, 196, 198, 203, 204, 207, 214, 201; 560/25, 29, 33, 45, 49, 60, 81, 87, 88, 105, 129, 160, 171, 180, 195, 197, 227

[56] References Cited

U.S. PATENT DOCUMENTS

| 3,970,586 | 7/1976 | Schliebs et al. | 252/355 |
| 4,602,092 | 7/1986 | Thottathil et al. | 560/105 |
| 4,824,886 | 4/1989 | Schmidt et al. | 524/131 |

FOREIGN PATENT DOCUMENTS

| 0238825 | 9/1987 | European Pat. Off. . |
| 2424243 | 11/1975 | Germany . |
| 2439281 | 2/1976 | Germany . |

OTHER PUBLICATIONS

Ullmann, Enzyklopädie der technischen Chemie, Fourth Edition, vol. 11, pp. 643–644 (1976).
Ullmann, Enzyklopädie der technischen Chemie, Fifth Edition, vol. A 11, pp. 373–374 (1988).
Ullman, Enzyklopädie der technischen Chemie, Fourth Edition, vol. 23, p. 87 (1983).
Ullman, Enzyklopädie der etchnischen Chemie, Fourth Edition, vol. 16, pp. 168–169 (1978).
J. N. Meussdoerffer and Hans Niederprüm, "Fluortenside and Fluorhaltige Phobiermittelgrenzflächenaktive Perfluorverbindungen", Chemiker-Zeitung, 104, pp. 45–52 (1980).

*Primary Examiner*—Paul J. Killos
*Assistant Examiner*—Dwayne C. Jones
*Attorney, Agent, or Firm*—Connolly & Hutz

[57] ABSTRACT

The present invention relates to fluorinated carboxylic acid esters of phosphono- and phosphinocarboxylic acids containing hydroxyl and/or mercapto groups, their use as waterproofing and/or oil-repellency agents, and a method for their preparation.

20 Claims, No Drawings

FLUORINATED CARBOXYLIC ACID ESTERS OF PHOSPHONO- AND PHOSPHINOCARBOXYLIC ACIDS CONTAINING HYDROXYL AND/OR MERCAPTO GROUPS, A METHOD FOR THEIR PREPARATION, AND THEIR USE

The present invention relates to fluorinated carboxylic acid esters of phosphono- and phosphinocarboxylic acids containing hydroxyl and/or mercapto groups, their use as waterproofing and/or oil-repellency agents, and a method for their preparation.

Compounds containing perfluoroalkyl groups are widely used in impregnation agents in industry due to their waterproofing and oil-repellency properties (see Ullmann, Enzyklopädie der technischen Chemie, Fourth Edition, 1976, Volume 11, page 644; and ibid, Fifth Edition, 1988, Volume A11, pages 373-374). Typical applications comprise their use as an impregnation agent for waterproofing and imparting oil-repellency to textiles (see Ullmann, Enzyklopädie der technischen Chemie, Fourth Edition, 1983, Volume 23, page 87), leather (see Ullmann, Enzyklopädie der technischen Chemie, Fourth Edition, 1978, Volume 16, page 168) and paper (see J. N. Meuβdoerffer and H. Niederprüm, Chemikerzeitung 104 (1980) 45–52).

Examples of proofing agents such as these comprise alcohols and acrylates containing perfluoro groups, or their polymer dispersions (see J. N. Meuβdoerffer and H. Niederprüm, Chemikerzeitung 104 (1980) 45–52; and Ullmann, Enzyklopädie der technischen Chemie, Fourth Edition, 1983, Volume 23, page 87). Routes for their synthesis are described by J. N. Meuβdoerffer and H. Niederprüm in Chemikerzeitung 104 (1980) 45–52.

The perfluorinated compounds used as starting materials in the above-mentioned fluorinated surfactants are produced industrially by three different routes:
a) electrochemical fluorination;
b) telomerization of perfluoroolefines, particularly tetrafluoroethylene; and
c) oligomerization of tetrafluoroethylene.

The above-mentioned methods of preparing perfluorinated starting materials are very expensive on an industrial scale, which results in high manufacturing costs for the desired chemical compounds containing perfluoro groups.

The object of the invention is to provide modified organic compounds containing fluoro groups which have waterproofing and/or oil-repellency properties, and which can be produced simply and inexpensively.

This object is achieved by means of the fluorinated carboxylic acid esters of phosphono- or phosphinocarboxylic acids containing hydroxyl and/or mercapto groups according to the invention.

The present invention relates to fluorinated carboxylic acid esters of phosphono- or phosphinocarboxylic acids containing hydroxyl and/or mercapto groups, of general formula (I):

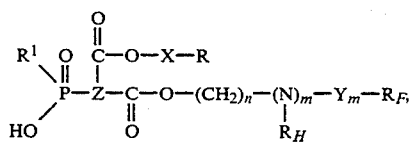

where $R^1$ is a hydroxyl group, a methyl group, an ethyl group or a phenyl radical, $R_F$ is a linear or branched fluoroalkyl radical with 1 to 18 carbon atoms, or a fluorinated, branched or linear monomeric ether or polyether with 1 to 18 carbon atoms, $R_H$ is a linear or branched alkyl radical with 1 to 10 carbon atoms, R is a hydroxyl or mercapto group, X represents a linear or branched alkylene radical with 1 to 20 carbon atoms, or a linear or branched alkylene radical with 1 to 20 carbon atoms and with one or more substituent R groups, where R has the same meaning as above, Y represents a

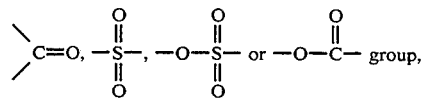

Z represents a linear or branched alkanetriyl radical (trivalent hydrocarbon radical) with 1 to 20 carbon atoms, or a linear or branched alkanetriyl radical with 1 to 20 carbon atoms, interrupted by amino groups which may themselves contain $C_1$ to $C_{10}$ alkyl groups or aryl groups as substituents, or a linear or branched alkanetriyl radical with 1 to 20 carbon atoms with one or more substituent groups of structure —$COR^2$, or a linear or branched alkanetriyl radical with 1 to 20 carbon atoms with one or more substituent groups of structure —$PO_2HR^1$ where $R^1$, has the same meaning as above, m may be 0 or 1, n is an integer from 0 to 6, and $R^2$ represents a hydroxyl radical, or a radical of structure

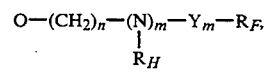

or a radical of structure O—X—R, or a linear or branched alkoxy radical with 1 to 30 carbon atoms, where n, m, $R_H$, $R_F$, R, X and Y have the same meaning as above, and their salts.

The fluorinated carboxylic acid esters of phosphono- or phosphinocarboxylic acids containing hydroxyl and/or mercapto groups are preferably those in which $R_F$ is a linear or branched fluoroalkyl radical with 3 to 10 carbon atoms.

Fluorinated carboxylic acid esters of phosphono- or phosphinocarboxylic acids containing hydroxyl and/or mercapto groups, in which $R_H$ represents an alkyl radical with one or two carbon atoms, are preferred.

Fluorinated carboxylic acid esters of phosphono- or phosphinocarboxylic acids containing hydroxyl and/or mercapto groups, in which n is one or two, are particularly preferred.

Fluorinated carboxylic acid esters of phosphono- or phosphinocarboxylic acids containing hydroxyl and/or mercapto groups, in which m is equal to one, are particularly preferred.

For example, particularly preferred fluorinated carboxylic acid esters of phosphono- or phosphinocarboxylic acids containing hydroxyl and/or mercapto groups have the following structure:

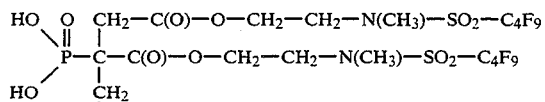

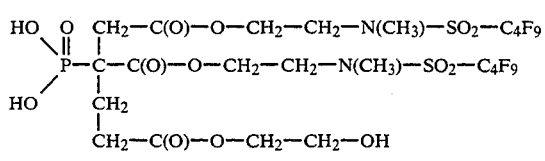

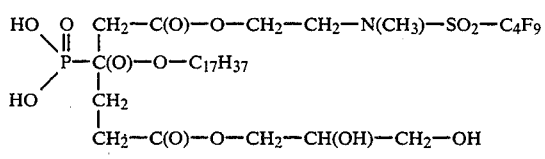

The radicals listed below are particularly preferred:
Examples of $R_F$:
$CF_3-(CF_2)_2-$
$CF_3-(CF_2)_3-$
$CF_3-(CF_2)_5-$
$CF_3-(CF_2)_6-$
$CF_3-(CF_2)_7-$
$CF_3-(CF_2)_{11}-$
$C_5F_5-$
$CF_3-C_6F_4-$
$H-(CF_2)_6-$
$H-(CF_2)_2-O-$
$CF_3-CHF-CF_2-O-$
$CF_2-CF_2-CF_2-O-CF(CF_3)-$
$CF_3-CF_2-[CF_2-O-CF(CF_3)]_2-$
$CF_3-CF_2-[CF_2-O-CF(CF_3)]_3-$
Examples of Z:

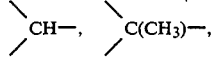

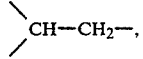

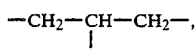

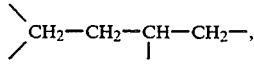

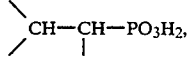

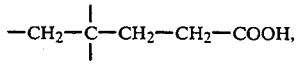

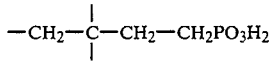

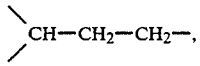

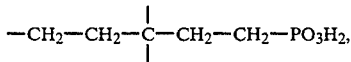

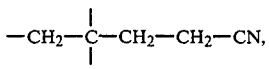

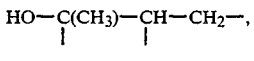

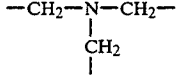

The fluorinated carboxylic acid esters of phosphono- or phosphinocarboxylic acids containing hydroxyl and/or mercapto groups-according to the invention may be prepared by multistage synthesis for example, employing esterification reactions of the corresponding phosphono- or phosphinocarboxylic acids or their salts with alcohols containing fluoro groups and polyhydric alcohols or hydroxyfunctional thiols:

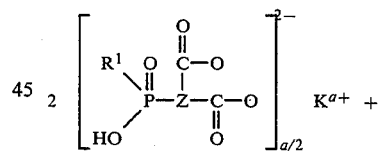

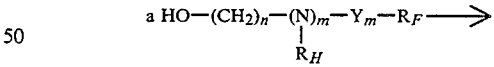

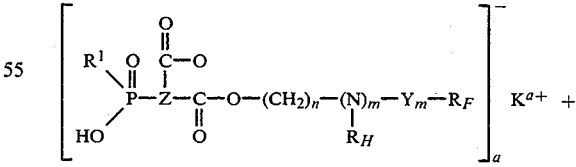

(HO)$_a$K

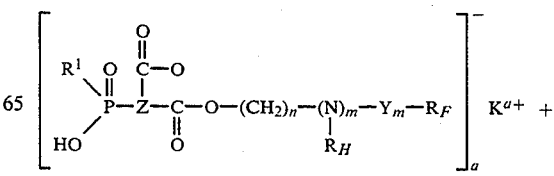

-continued $$a\ HO-X-R \longrightarrow$$

$$\begin{array}{c} R^1 \diagdown \overset{O}{\underset{\parallel}{P}}\diagup \overset{O}{\underset{\parallel}{C}}-O-X-R \\ HO \diagup \overset{}{\underset{}{P}}-Z-\overset{}{\underset{\parallel}{C}}-O-(CH_2)_n-(N)_m-Y_m-R_F + (HO)_aK \\ \phantom{HO}\quad O \qquad\quad \underset{R_H}{|} \end{array}$$

where $R^1$, R, $R_F$, $R_H$, X, Y, Z, m and n have the same meaning as above,

K is a hydrogen cation, an ammonium cation or a monovalent or polyvalent metal cation, and a is an integer which corresponds to the charge of the cation K.

The present invention also relates to the use of the fluorinated carboxylic acid esters of phosphono- or phosphinocarboxylic acids containing hydroxyl and/or mercapto groups according to the invention as waterproofing agents and/or oil-repellency agents.

Due to the waterproofing and oil-repellency properties of the compounds according to the invention, they may be used as impregnating agents in various areas of application, wherein the compounds according to the invention may be applied as such or in the form of polymer dispersions, for example.

For example, the compounds according to the invention may be used on natural and synthetic fibres (e.g. for textiles, carpets or awnings) to repel water, grease, oil and/or dirt.

The compounds according to the invention may also be used on paper and cardboard (e.g. for packaging or fleeces) to repel water, grease, oil and/or dirt.

Moreover, the compounds according to the invention may be used on leather (e.g. for upholstery, shoes or clothing) to repel water, grease, oil and/or dirt.

The compounds according to the invention may also be used on ceramics (e.g. tiles), on natural or artificial stone (e.g. sandstone), on wood (e.g. the wooden cladding of facades) and on plastics (e.g. polyesters) for impregnation against water, grease, oil, dirt, algae growth and/or weathering.

The invention will be described in more detail by means of the following examples.

EXAMPLES

Example 1

N-(2-hydroxyethyl)-N-methyl-perfluorobutyl sulphonamide (1.0 mole/357 g) was dissolved in 4-methyl-pentane-2-one (200 ml) in a three-necked flask fitted with a stirrer and a water trap, and concentrated sulphuric acid (0.5 ml) was added. This solution was heated to about 116° C. 2-phosphonobutane-1,2,4-tricarboxylic acid (0.5 mole/135 g) dissolved in water (135 g) was then slowly added. After the addition was complete, the reaction mixture was refluxed with stirring until the entire amount of water (153 ml) had been distilled off.

Ethanediol (0.5 mole/31 g) was then slowly added, followed by refluxing with stirring until the entire amount of water (9 ml) had been distilled off from the reaction mixture.

After the reaction was complete, the solvent was distilled off at 70° C. and 70 mbar, and the product obtained was completely dried. The yield of 2-phosphonobutane-1,2,4-tricarboxylic acid which was triple-esterified with two equivalents of N-(2-hydroxyethyl)-N-methyl-perfluorobutyl sulphonamide and one equivalent of ethanediol was 491 g (98.9% theoretical).

Example 2

N-(2-hydroxyethyl)-N-methyl-perfluorobutyl sulphonamide (0.6 mole/214 g) was dissolved in 4-methyl-pentane-2-one (150 ml) in a three-necked flask fitted with a stirrer and a water trap, and concentrated sulphuric acid (0.5 ml) was added. This solution was heated to about 116° C. 2-phosphonobutane-1,2,4-tricarboxylic acid (0.3 mole/81 g) dissolved in water (81 g) was then slowly added. After the addition was complete, the reaction mixture was refluxed with stirring until the entire amount of water (91.8 ml) had been distilled off.

Propanetriol (0.3 mole/28 g) was then slowly added, followed by refluxing with stirring until the entire amount of water (3.6 ml) had been distilled off from the reaction mixture.

After the reaction was complete, the solvent was distilled off at 70° C. and 70 mbar, and the product obtained was completely dried. The yield of 2-phosphonobutane-1,2,4-tricarboxylic acid which was triple-esterified with two equivalents of N-(2-hydroxyethyl)-N-methyl-perfluorobutyl sulphonamide and one equivalent of propanetriol was 305 g (99.5 % theoretical).

Example 3

N-(2-hydroxyethyl)-N-methyl-perfluorooctyl sulphonamide (0.1 mole/56 g) was dissolved in 4-methyl pentane-2-one (150 ml) in a three-necked flask fitted with a stirrer and a water trap, and concentrated sulphuric acid (0.5 ml) was added. This solution was heated to about 116° C. 2-phosphonobutane-1,2,4-tricarboxylic acid (0.1 mole/27 g) dissolved in 27 g of water was then slowly added. After the addition was complete, the reaction mixture was refluxed with stirring until the entire amount of water (28.8 ml) had been distilled off.

Octadecanol (0.1 mole/28 g) dissolved in 50 ml of 4-methyl-pentane-2-one was then slowly added, followed by refluxing with stirring until the entire amount of water (1.8 ml) had been distilled off from the reaction mixture.

Ethanediol (0.1 mole/6 g) was then slowly added, and the reaction mixture was refluxed with stirring until the entire amount of water (1.8 ml) had been distilled off.

After the reaction was complete, the solvent was distilled off at 70° C. and 70 mbar, and the product obtained was completely dried. The yield of 2-phosphonobutane-1,2,4-tricarboxylic acid which was triple-esterified with one equivalent each of N-(2-hydroxyethyl)-N-methyl-perfluorooctyl sulphonamide, octadecanol and ethanediol was 109 g (98.8 % theoretical).

What is claimed is:

1. Fluorinated carboxylic acid esters of phosphono- or phosphinocarboxylic acids containing hydroxyl and/or mercapto groups, of general formula (I)

$$\begin{array}{c} R^1 \diagdown \overset{O}{\underset{\parallel}{P}}\diagup \overset{O}{\underset{\parallel}{C}}-O-X-R \\ HO \diagup \overset{}{\underset{}{P}}-Z-\overset{}{\underset{\parallel}{C}}-O-(CH_2)_n-(N)_m-Y_m-R_F, \\ \phantom{HO}\quad O \qquad\quad \underset{R_H}{|} \end{array} \qquad (I)$$

where:
- $R^1$ is a hydroxyl group, a methyl group, an ethyl group or a phenyl radical,
- $R_F$ is a linear or branched fluoroalkyl radical with 1 to 18 carbon atoms, or a fluorinated branched or linear monomeric ether or polyether with 1 to 18 carbon atoms,
- $R_H$ is a linear or branched alkyl radical with 1 to 10 carbon atoms,
- R is a hydroxyl or a mercapto group,
- X represents a linear or branched alkylene radical with 1 to 20 carbon atoms, or a linear or branched alkylene radical with 1 to 20 carbon atoms and with one or more substituent R groups, where R has the same meaning as above,
- Y represents a

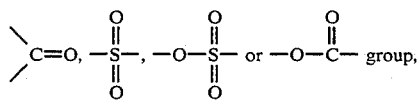

Z represents a linear or branched alkanetriyl radical (trivalent hydrocarbon radical) with 1 to 20 carbon atoms, or a linear or branched alkanetriyl radical with 1 to 20 carbon atoms with one or more substituent groups of structure —$COR^2$, or a linear or branched alkanetriyl radical with 1 to 20 carbon atoms with one or more substituent groups of structure —$PO_2HR^1$, where $R^1$ has the same meaning as above,
- m is 0 or 1,
- n is an integer from 0 to 6, and
- $R^2$ represents a hydroxyl radical, or a radical of structure

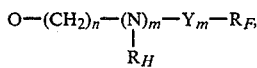

or a radical of structure O—X—R, or a linear or branched alkoxy radical with 1 to 30 carbon atoms, where n, m, $R_H$, $R_F$,
R, X and Y have the same meaning as above, and their salts.

2. Fluorinated carboxylic acid esters of phosphono- or phosphinocarboxylic acids containing hydroxyl and/or mercapto groups according to claim 1, wherein $R_F$ is a linear or branched fluoroalkyl radical with 3 to 10 carbon atoms.

3. Fluorinated carboxylic acid esters of phosphono- or phosphinocarboxylic acids containing hydroxyl and/or mercapto groups according to claim 1, wherein $R_H$ represents an alkyl radical with one or two carbon atoms.

4. Fluorinated carboxylic acid esters of phosphono- or phosphinocarboxylic acids containing hydroxyl and/or mercapto groups according to claim 1, wherein n is one or two.

5. Fluorinated carboxylic acid esters of phosphono- or phosphinocarboxylic acids containing hydroxyl and/or mercapto groups according to claim 1, wherein m is equal to one.

6. A method of preparing the fluorinated carboxylic acid esters of phosphono- or phosphinocarboxylic acids containing hydroxyl and/or mercapto groups according to claim 1, wherein said method comprises a multistage synthesis and further wherein the corresponding phosphono- or phosphinocarboxylic acids of formula (II)

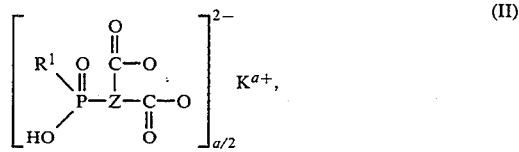

or their salts,
where K is a hydrogen cation, an ammonium cation or a monovalent or polyvalent metal cation, a is an integer which corresponds to the charge of the cation K, and $R^1$ and Z have the same meaning as in claim 1,
are esterified in a first step with the corresponding alcohols, containing fluoro groups and of formula (III)

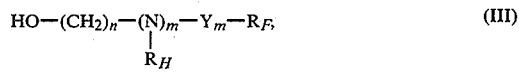

where n, m, $R_H$, Y and $R_F$ have the same meaning as in claim 1, and, in a further step, the ester formed in the first step is esterified with the corresponding polyhydric alcohols or hydroxyfunctional thiols of formula (IV)

$$HO-X-R \quad (IV),$$

where X and R have the same meaning as in claim 1.

7. Fluorinated carboxylic acid esters of phosphonocarboxylic acids containing hydroxyl and/or mercapto groups according to claim 1, wherein said esters have the following formula:

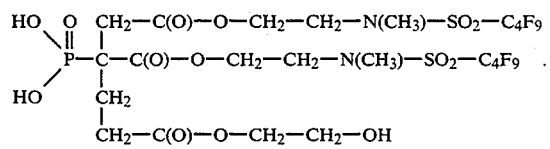

8. Fluorinated carboxylic acid esters of phosphonocarboxylic acids containing hydroxyl and/or mercapto groups according to claim 1, wherein said esters have the following formula:

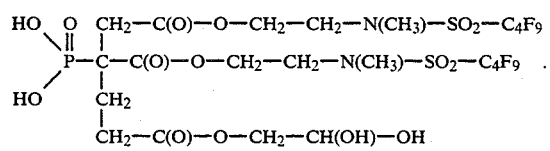

9. Fluorinated carboxylic acid esters of phosphonocarboxylic acids containing hydroxyl and/or mercapto groups according to claim 1, wherein said esters have the following formula:

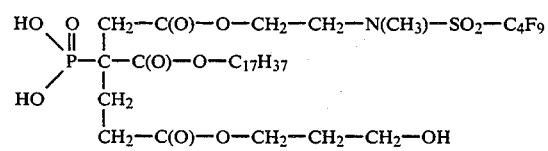

10. Fluorinated carboxylic acid esters of phosphono- or phosphinocarboxylic acids containing hydroxyl and- /or mercapto groups according to claim 1, wherein $R_F$ is a radical selected from the group consisting of:

$CF_3$—$(CF_2)_2$—
$CF_3$—$(CF_2)_3$—
$CF_3$—$(CF_2)_5$—
$CF_3$—$(CF_2)_6$—
$CF_3$—$(CF_2)_7$—
$CF_3$—$(CF_2)_{11}$—
$C_5F_5$—
$CF_3$—$C_6F_4$—
H—$(CF_2)_6$—
H—$(CF_2)_2$—O—
$CF_3$—CHF—$CF_2$—O—
$CF_2$—$CF_2$—$CF_2$—O—CF $(CF_3)$—
$CF_3$—$CF_2$—[$CF_2$—O—CF $(CF_3)$]$_2$—, and
$CF_3$—$CF_2$—[$CF_2$—O—CF $(CF_3)$]$_3$—.

11. Fluorinated carboxylic acid esters of phosphono- or phosphinocarboxylic acids containing hydroxyl and- /or mercapto groups according to claim 1, wherein Z is a radical selected from the group consisting of

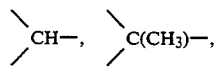

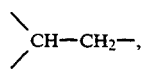

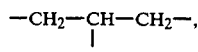

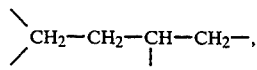

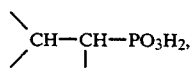

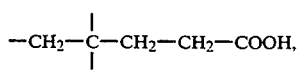

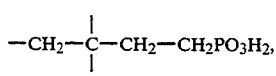

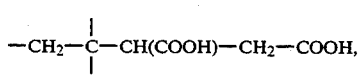

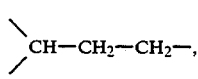

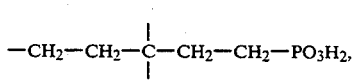

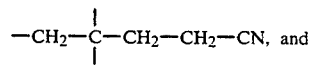

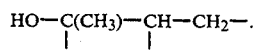

12. Fluorinated carboxylic acid esters of phosphono- or phosphinocarboxylic acids containing hydroxyl and- /or mercapto groups, of general formula (I)

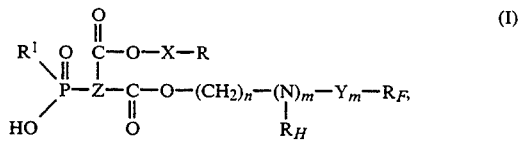

(I)

where:
$R^1$ is a hydroxyl group, a methyl group, an ethyl group or a phenyl radical,
$R_F$ is a linear or branched fluoroalkyl radical with 1 to 18 carbon atoms, or a fluorinated branched or linear monomeric ether or polyether with 1 to 18 carbon atoms,
$R_H$ is a linear or branched alkyl radical with 1 to 10 carbon atoms,
R is a hydroxyl or a mercapto group,
X represents a linear or branched alkylene radical with 1 to 20 carbon atoms, or a linear or branched alkylene radical with 1 to 20 carbon atoms and with one or more substituent R groups, where R has the same meaning as above,
Y represents a

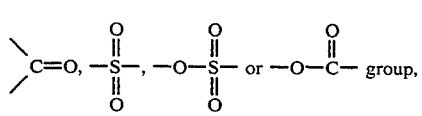

Z represents a linear or branched alkanetriyl radical (trivalent hydrocarbon radical) with 1 to 20 carbon atoms, and further wherein said alkanetriyl radical is interrupted by an amino group which may contain $C_1$ to $C_{10}$ alkyl groups or aryl groups as substituents
m is 0 or 1, and
n is an integer from 0 to 6,
and their salts.

13. Fluorinated carboxylic acid esters of phosphono- or phosphinocarboxylic acids containing hydroxyl and- /or mercapto groups according to claim 12, wherein $R_F$ is a linear or branched fluoroalkyl radical with 3 to 10 carbon atoms.

14. Fluorinated carboxylic acid esters of phosphono- or phosphinocarboxylic acids containing hydroxyl and- /or mercapto groups according to claim 12, wherein $R_H$ represents an alkyl radical with one or two carbon atoms.

15. Fluorinated carboxylic acid esters of phosphono- or phosphinocarboxylic acids containing hydroxyl and- /or mercapto groups according to claim 12, wherein n is one or two.

16. Fluorinated carboxylic acid esters of phosphono- or phosphinocarboxylic acids containing hydroxyl and- /or mercapto groups according to claim 12, wherein m is equal to one.

17. A method of preparing the fluorinated carboxylic acid esters of phosphono- or phosphinocarboxylic acids containing hydroxyl and/or mercapto groups according to claim 13, wherein said method comprises a multistage synthesis and further wherein the corresponding phosphono- or phosphinocarboxylic acids of formula (II)

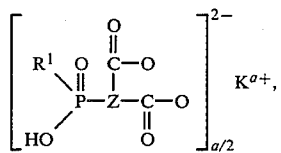

or their salts,
where K is a hydrogen cation, an ammonium cation or a monovalent or polyvalent metal cation, a is an integer which corresponds to the charge of the cation K, and $R^1$ and Z have the same meaning as in claim 13, are esterified in a first step with the corresponding alcohols, containing fluoro groups and of formula (III)

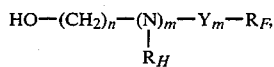

where n, m, $R_H$, Y and $R_F$ have the same meaning as in claim 13, and, in a further step, the ester formed in the first step is esterified with the corresponding polyhydric alcohols or hydroxyfunctional thiols of formula (IV)

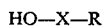   (IV), where X and R have the same meaning as in claim 12.

18. Fluorinated carboxylic acid esters of phosphono- or phosphinocarboxylic acids containing hydroxyl and/or mercapto groups according to claim 12, wherein $R_F$ is a radical selected from the group consisting of:

$CF_3-(CF_2)_2-$
$CF_3-(CF_2)_3-$
$CF_3-(CF_2)_5-$
$CF_3-(CF_2)_6-$
$CF_3-(CF_2)_7-$
$CF_3-(CF_2)_{11}-$
$C_5F_5-$
$CF_3-C_6F_4-$
$H-(CF_2)_6-$
$H-(CF_2)_2-O-$
$CF_3-CHF-CF_2-O-$
$CF_2-CF_2-CF_2-O-CF(CF_3)-$
$CF_3-CF_2-[CF_2-O-CF(CF_3)]_2-$, and
$CF_3-CF_2-[CF_2-O-CF(CF_3)]_3-$.

19. Fluorinated carboxylic acid esters of phosphono- or phosphinocarboxylic acids containing hydroxyl and/or mercapto groups according to claim 12, wherein Z represents a linear or branched alkanetriyl radical (trivalent hydrocarbon radical) with 1 to 20 carbon atoms, and further wherein said alkanetriyl radical is interrupted by an amino group which may contain $C_1$ to $C_{10}$ alkyl groups or aryl groups as substituents.

20. Fluorinated carboxylic acid esters of phosphono- or phosphinocarboxylic acids containing hydroxyl and/or mercapto groups according to claim 19, wherein Z is

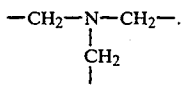

* * * * *

UNITED STATES PATENT AND TRADEMARK OFFICE
CERTIFICATE OF CORRECTION

PATENT NO. : 5,424,474
DATED : June 13, 1995
INVENTOR(S) : Pohner et al.

It is certified that error appears in the above-indentified patent and that said Letters Patent is hereby corrected as shown below:

Column 11, lines 6, 22, and 31, "claim 13" should be --claim 12--.

Signed and Sealed this

Thirteenth Day of August, 1996

Attest:

BRUCE LEHMAN

Attesting Officer          Commissioner of Patents and Trademarks